United States Patent
Jayasundara et al.

(10) Patent No.: US 12,024,802 B2
(45) Date of Patent: Jul. 2, 2024

(54) TEXTILE AND MANUFACTURING METHOD THEREOF

(71) Applicant: MAS INNOVATION (PRIVATE) LIMITED, Colombo (LK)

(72) Inventors: Jayasundara Walpola Kankanamalage Kosalasiri Jayasundara, Colombo (LK); Hetti Arachchige Malaka Chathuranga Perera, Colombo (LK); Thennakonge Maduka Sampath Chandrasiri, Colombo (LK); Kukaraj Tharmasegaram, Colombo (LK)

(73) Assignee: MAS INNOVATION (PRIVATE) LIMITED, Battaramulla (LK)

( * ) Notice: Subject to any disclaimer, the term of this patent is extended or adjusted under 35 U.S.C. 154(b) by 672 days.

(21) Appl. No.: 16/768,721

(22) PCT Filed: Nov. 30, 2018

(86) PCT No.: PCT/SG2018/050588
§ 371 (c)(1),
(2) Date: Jun. 1, 2020

(87) PCT Pub. No.: WO2019/108138
PCT Pub. Date: Jun. 6, 2019

(65) Prior Publication Data
US 2021/0172101 A1 Jun. 10, 2021

(30) Foreign Application Priority Data
Dec. 1, 2017 (SG) .......................... 10201710003Y

(51) Int. Cl.
*D04B 1/16* (2006.01)
*A41D 1/22* (2018.01)
(Continued)

(52) U.S. Cl.
CPC ................ *D04B 1/16* (2013.01); *A41D 1/22* (2013.01); *A41D 19/00* (2013.01); *D02G 3/12* (2013.01);
(Continued)

(58) Field of Classification Search
CPC ... D04B 1/16; D04B 1/14; A41D 1/22; A41D 19/00; A41D 2400/12; A41D 2500/10;
(Continued)

(56) References Cited

U.S. PATENT DOCUMENTS 6,854,296 B1 * 2/2005 Miller, III ................ D04B 1/22
66/196
2008/0223844 A1 9/2008 Cronn
(Continued)

FOREIGN PATENT DOCUMENTS

WO 2014138204 A1 9/2014
WO WO-2016118746 A1 * 7/2016 ............... D02G 3/32

OTHER PUBLICATIONS

International Search Report issued in International Application No. PCT/SG2018/050588 dated Feb. 13, 2019 (4 pages).
(Continued)

*Primary Examiner* — Shawntina T Fuqua
(74) *Attorney, Agent, or Firm* — Osha Bergman Watanabe & Burton LLP

(57) ABSTRACT

The present disclosure generally relates to a textile (100) and a manufacturing method (200) thereof. The textile (100) comprises: a fabric body (102) formed from one or more types of yarns; a continuous channel (104) formed within the fabric body (102); and an insulated conductive element (106) disposed within the continuous channel (104), wherein the textile (100) is heatable in response to electrical current being conducted through the insulated conductive element (106).

17 Claims, 9 Drawing Sheets

(51) Int. Cl.
   *A41D 19/00* (2006.01)
   *D02G 3/12* (2006.01)
   *D02G 3/44* (2006.01)
   *H05B 3/34* (2006.01)

(52) U.S. Cl.
   CPC .............. *D02G 3/441* (2013.01); *H05B 3/342* (2013.01); *A41D 2400/12* (2013.01); *A41D 2500/10* (2013.01); *D10B 2401/16* (2013.01)

(58) Field of Classification Search
   CPC ...... A41D 13/0051; D02G 3/12; D02G 3/441; H05B 3/342; D10B 2401/16; A41C 1/08
   See application file for complete search history.

(56) References Cited

U.S. PATENT DOCUMENTS

| | | | | |
|---|---|---|---|---|
| 2010/0154918 A1* | 6/2010 | Li | ............................ | D04B 1/14 139/412 |
| 2017/0145596 A1* | 5/2017 | Hays | ........................ | A47C 7/24 |
| 2018/0195985 A1* | 7/2018 | Nebuya | .................. | G01N 27/02 |
| 2019/0208862 A1* | 7/2019 | Poegl | ................... | A43B 23/042 |
| 2022/0119990 A1* | 4/2022 | Hu | ........................... | D02G 3/26 |

OTHER PUBLICATIONS

Written Opinion issued in International Application No. PCT/SG2018/050588 dated Feb. 13, 2019 (6 pages).

Dias, T., Smart Textiles—Adding Value to Sri Lankan Textiles The Electronic Textiles Option, 2009_published online on Nov. 17, 2009 (55 pages).

Nottingham Trent University, Impact (REF3a/b), 34—Art and Design: History, Practice and Theory, Advanced Textiles case study, 2014_published online on Dec. 18, 2014 (4 pages).

Office Action issued in corresponding EP Application No. 18821769.9 dated Apr. 16, 2021 (6 pages).

* cited by examiner

TEXTILE AND MANUFACTURING METHOD THEREOF

CROSS REFERENCE TO RELATED APPLICATIONS

The present disclosure claims the benefit of Singapore Patent Application No. 10201710003Y filed on 1 Dec. 2017, which is incorporated in its entirety by reference herein.

TECHNICAL FIELD

The present disclosure generally relates to a textile and a manufacturing method thereof. More particularly, the present disclosure describes various embodiments of a heatable textile, as well as a method of manufacturing the heatable textile.

BACKGROUND

Various types of textiles have been used for producing garments and clothing. Particularly for people living in temperate climates, some of these garments have heating capabilities to provide warmth to users or wearers during cold winters. Such garments are made of textiles with heating panels or regions which are usually electrically powered to provide the heating capabilities. The heating panels are developed separately and then stitched onto the fabric body of the textiles. Specifically, the fabric bodies of the textiles are formed first and the heating panels are later placed on top of the fabric bodies for subsequent stitching. There are many separate steps or operations to integrate the heating panels with the fabric bodies, and also many interconnection points of the heating panels in the textiles during stitching thereof, resulting in safety issues such as short circuit risks. To mitigate the short circuit risks which could potentially cause electrical injuries to the wearer, some textiles include another layer of fabric or insulation material over the heating panels. However, the additional layer of fabric or insulation material reduces the breathability or air permeability of the textiles, likely causing discomfort to the wearer.

Therefore, in order to address or alleviate at least one of the aforementioned problems and/or disadvantages, there is a need to provide a textile and a manufacturing method thereof, in which there is at least an improvement and/or advantage over the prior art.

SUMMARY

According to a first aspect of the present disclosure, there is a textile comprising: a fabric body formed from one or more types of yarns; a continuous channel formed within the fabric body; and an insulated conductive element disposed within the continuous channel, wherein the textile is heatable in response to electrical current being conducted through the insulated conductive element.

According to a second aspect of the present disclosure, there is a method of manufacturing a textile, the method comprising: forming a fabric body from one or more types of yarns; forming a continuous channel within the fabric body; and disposing an insulated conductive element within the continuous channel, wherein the textile is heatable in response to electrical current being conducted through the insulated conductive element.

An advantage of the present disclosure is that the textile is heatable when electrical current flows through the insulated conductive element. The textile may thus be referred to a heating textile and may be used in garments. When a user wears a garment made of the textile, the textile is heatable to provide thermal comfort to the user, especially during cold or winter seasons.

A textile and a manufacturing method thereof according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. The recitation of a particular numerical value or value range herein is understood to include or be a recitation of an approximate numerical value or value range.

For purposes of brevity and clarity, descriptions of embodiments of the present disclosure are directed to a textile and a manufacturing method thereof, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, known systems, methods, procedures, and components have not been described in detail so as to not unnecessarily obscure aspects of the embodiments of the present disclosure.

Figure 1:
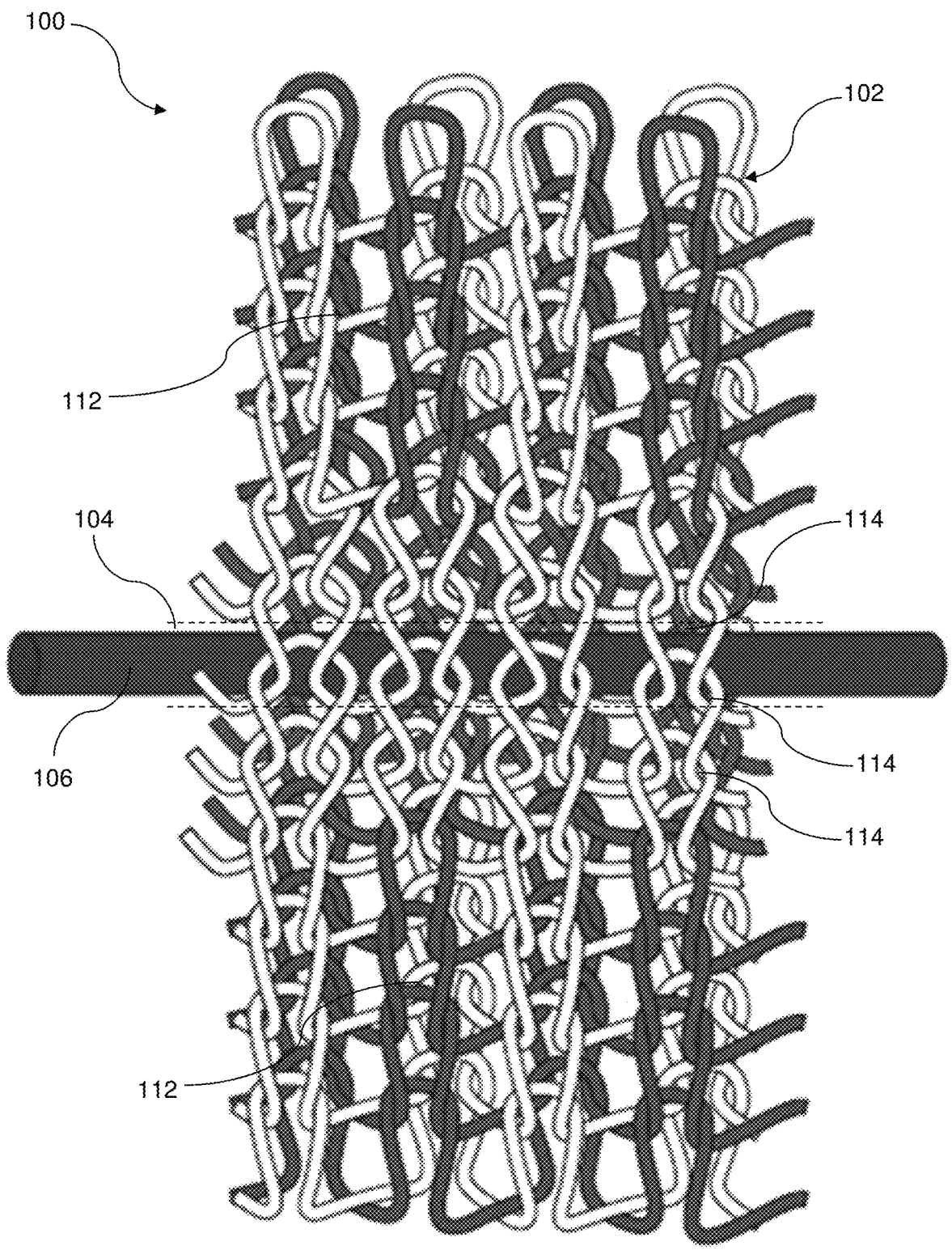
FIG. 1 is an illustration of a front view of the textile, in accordance with embodiments of the present disclosure.
Figure 2:
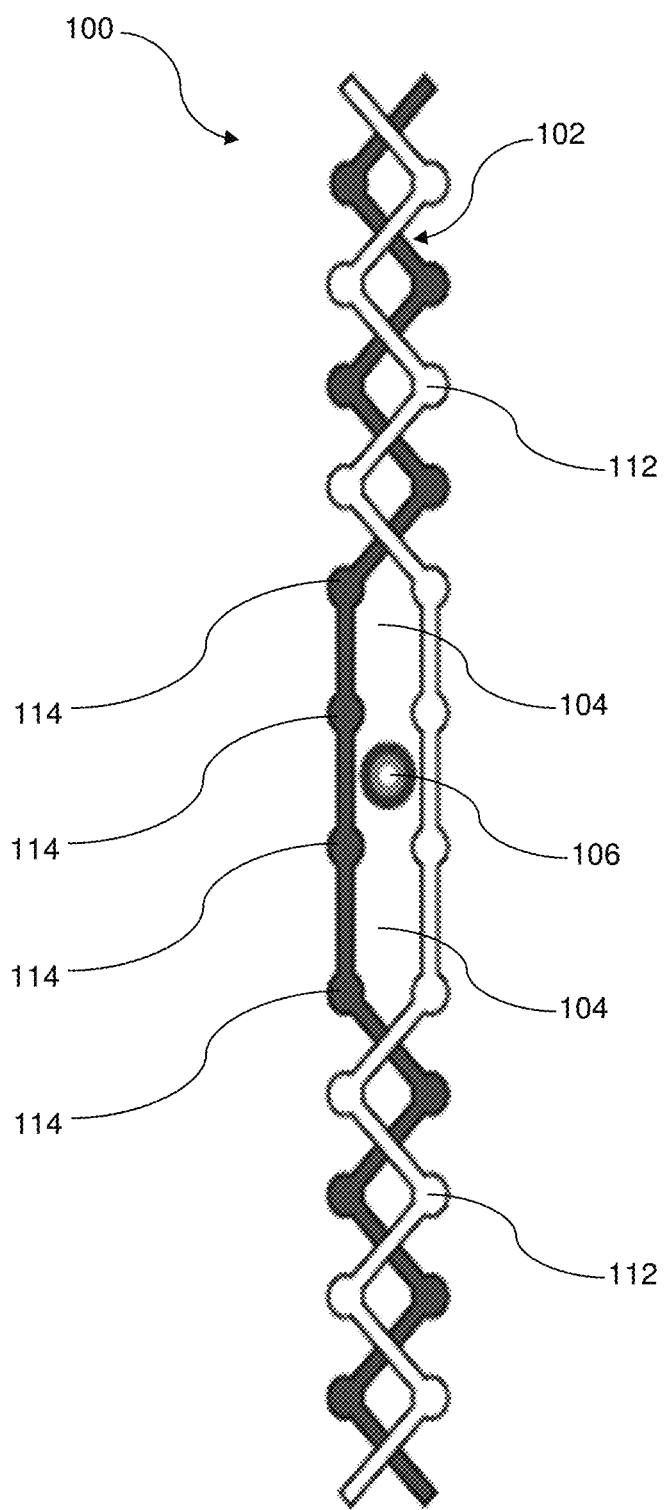
FIG. 2 is an illustration of a side view of the textile, in accordance with embodiments of the present disclosure.

In representative or exemplary embodiments of the present disclosure, there is a textile 100 as illustrated in FIG. 1 and FIG. 2. As used herein, the term "textile" is defined as a flexible material with a network or an interlacing of fibres, yarns, threads, or any combination thereof. The textile 100 may be used for producing other goods, particularly garments or clothing for wearing. There may be other applications or uses of the textile 100, such as but not limited to, car seats, compression sleeves, pouches, beddings, pillows, mattresses, shoes, gloves, medical accessories, health-related or wellness accessories, therapeutic accessories, warming mechanisms (e.g. for liquid containers, etc.

The textile 100 is made from a fabric and comprises a fabric body 102 formed from one or more types of yarns. As used herein, the term "fabric" is defined as a woven material made by weaving, knitting, knotting, spreading, crocheting, bonding, or any combination thereof, or a non-woven material made by braiding, felting, twisting, or any combination thereof. The method of making the fabric may vary according to the end application of the textile 100. Some examples include weft knit (flat bed and circular) and warp knit (lace manufacturing and fabric manufacturing methods). As used herein, the term "yarn" is defined as a continuous length of interlocked fibres. A yarn may be produced by spinning raw fibres of materials such as but not limited to wool, flax, cotton, or hemp to produce long strands.

In some embodiments, the one or more types of yarns forming the fabric body 102 comprises a passive heating yarn and/or a normal yarn. The passive heating yarn may be or comprises an infrared yarn and/or a yarn made of a phase change material. A phase change material is a substance with a high latent heat of fusion, such that the phase change material is capable of storing and releasing energy when melting and solidifying. Specifically, heat is released when the phase change material changes from the liquid phase to the solid phase.

Some examples of a passive heating yarn include, but not limited to, NILIT® heat yarn which integrates coffee charcoal into yarn for natural insulation, Resistex® Bioceramic yarn which absorbs body heat and emits as FLIR (forward looking infrared) rays, and Celliant fibre which uses minerals to convert body heat into infrared energy and reflect it back into the body. The normal yarn may be or comprises one or more of nylon yarn, polyester yarn, and spandex yarn.

In one embodiment, the fabric body 102 is formed from only the passive heating yarn. The passive heating yarn has some heat generation or heat retention characteristics or properties. The passive heating yarn may thus also be referred to as a thermal insulative/resistive yarn. A person wearing a garment or clothing made of the passive heating yarn will feel warm to a certain level due to heat retention from the person's body heat. Specifically, the characteristics or properties of the passive heating yarn traps or retains the heat emitted from the person's body, thereby keeping the person warm, even in the absence of any power source or other heating elements.

In another embodiment, the fabric body 102 is formed from a combination or blend of the passive heating yarn and the normal yarn. In yet another embodiment, the fabric body 102 is formed from a combination or blend of the passive heating yarn and a thermal conductive yarn. Specifically, the outer layer of the fabric body 102, i.e. the layer exposed to the environment, is made of the passive heating yarn or thermal insulative/resistive yarn. The inner layer of the fabric body 102, i.e. the layer in contact with the person's body, is made of the thermal conductive yarn. The thermal conductive yarn has good thermal conductivity which enables more heat transfer to the wearer and less heat transfer to the environment. Specifically, the person's body heat is more efficiently transferred from the inner layer (thermal conductive yarn) to the outer layer (passive heating yarn), and the heat is trapped or retained by the outer layer, thereby keeping the person warm.

The textile 100 further comprises a continuous channel 104 formed within the fabric body 102, and an insulated conductive element 106 disposed within the continuous channel 104. Specifically, the insulated conductive element 106 has an elongated profile and is laid or inserted inside the continuous channel 104. The textile 100 is heatable in response to electrical current being conducted through the insulated conductive element 106. Thus, the insulated conductive element 106 functions as an active heating element for heating the textile 100.

Figure 3:
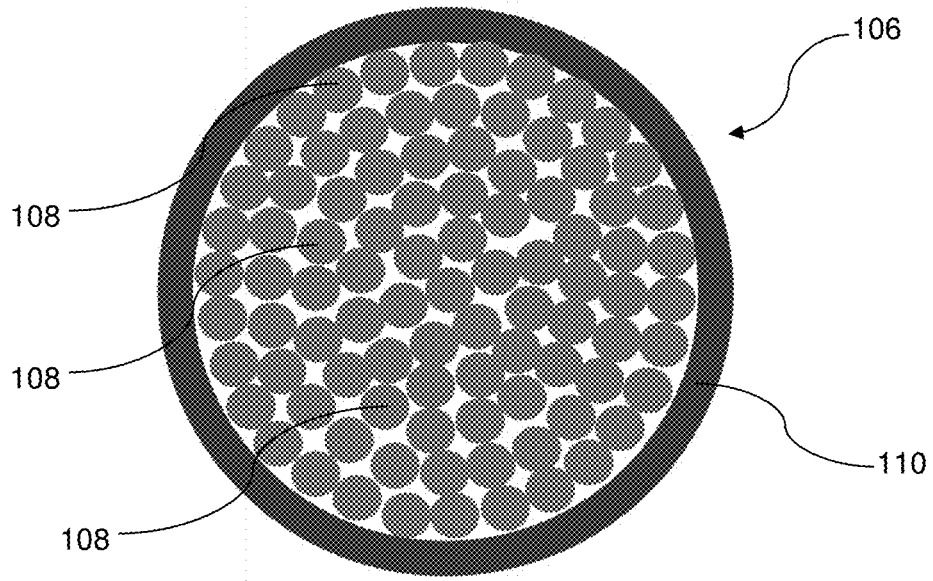
FIG. 3 is an illustration of a cross-sectional view of an insulated conductive element of the textile, in accordance with embodiments of the present disclosure.

With reference to FIG. 3, the insulated conductive element 106 includes a plurality of electrical conductive wires or filaments 108 bunched or braided together. The textile 100 is heatable from the heat generated by the insulated conductive element 106. Specifically, the insulated conductive element 106 heats up when the electrical current flows through the electrical conductive wires 108. This way of heating is also known as resistive heating. The electrical conductive wires 108 may be made of a copper material and may optionally be coated with a tin material. The electrical conductive wires 108 may be made of other materials such as, but not limited to, silver yarn/fibre/filament/wire, stainless steel yarn/fibre/filament/wire, carbon fibre, or other materials that can be used for resistive heating.

The insulated conductive element 106 includes an electrical insulation layer 110 as the outermost layer encapsulating the electrical conductive wires 108. The electrical insulation layer 110 may be made of an electrical insulation material that is able to withstand high temperatures and is non-flammable. Some examples of the electrical insulation material include, but are not limited to, silicone, fluorinated ethylene propylene (FEP), Teflon, nylon, or polyurethane, etc. The electrical insulation material 110 provides a safety feature for wearers of garments made of the textile 100 as the fabric body 102 is in contact with the wearer's body skin and the insulated conductive element 106 is potentially in contact with the body skin. The electrical insulation layer 110 reduces risk of electrical injuries to the wearer, as well as risk of the insulated conductive element 106 and/or the textile 100 catching fire when the insulated conductive element 106 is heated.

In one embodiment, the insulated conductive element 106 includes a nylon layer added into the core of the insulated conductive element 106. The nylon layer may be formed from wires or filaments of a nylon material bunched or braided together. The nylon layer may reside in the innermost core region of the insulated conductive element 106, such that the electrical conductive wires 108 encapsulate/surround the inner nylon core, e.g. by braiding around the inner nylon core. The inner nylon core provides cushioning for the electrical conductive wires 108 so that they have better flexibility and strain relief, thereby enhancing the reliability of the insulated conductive element 106. In another embodiment, the electrical conductive wires 108 reside in the innermost core region of the insulated conductive element 106, and the additional nylon layer encapsulates the electrical conductive wires 108. Other materials may be inserted into the innermost core region, such as but not limited to, aramids, Kevlar®, or Nomex®.

Figure 4:
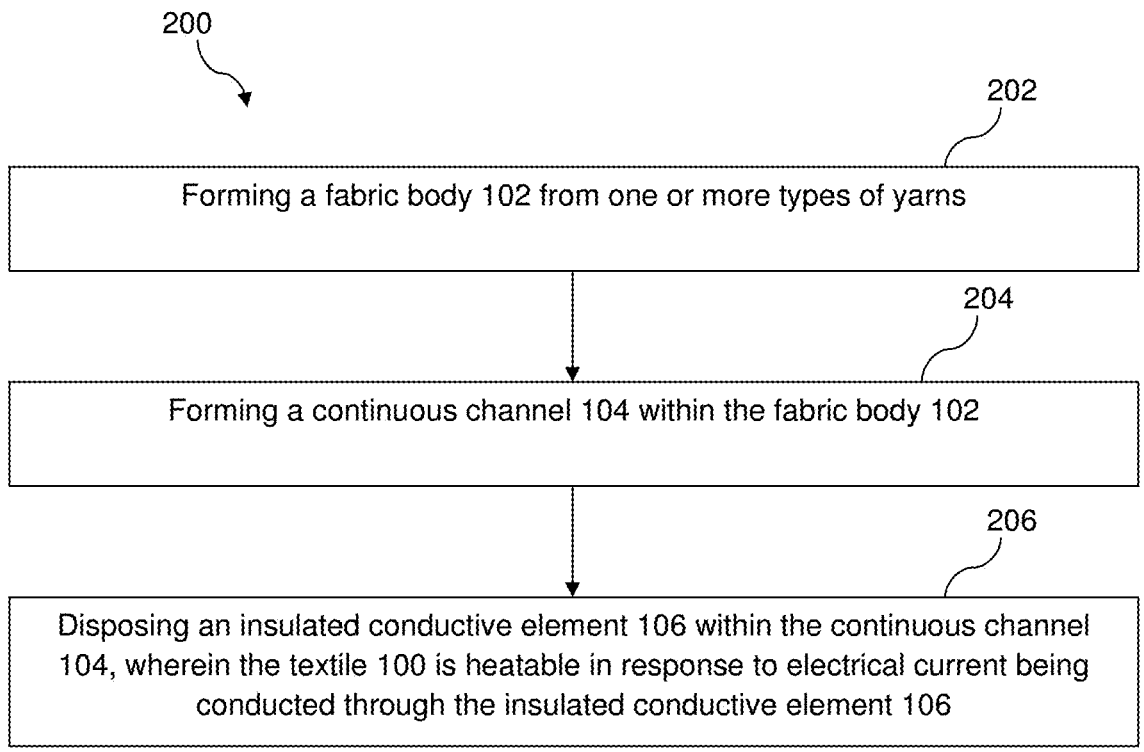
FIG. 4 is a flowchart illustration of a method of manufacturing the textile, in accordance with embodiments of the present disclosure.

In various embodiments with reference to FIG. 4, there is a method 200 of manufacturing a textile 100. Broadly, the method 200 comprises:

(a) a step 202 of forming a fabric body 102 from one or more types of yarns;

(b) a step 204 of forming a continuous channel 104 within the fabric body 102; and (c) a step 206 of disposing an insulated conductive element 106 within the continuous channel 104, wherein the textile 100 is heatable in response to electrical current being conducted through the insulated conductive element 106.

In some embodiments, in the steps 202 and 204, each of the fabric body 102 and the continuous channel 104 is formed by knitting, such as weft or warp knitting, from the one or more types of yarns as described above. The fabric body 102 may be formed or knitted by a double jersey knitting process. The continuous channel 104 may be formed or knitted within the fabric body 102 by a single jersey knitting process and during said forming or knitting of the fabric body 102. FIG. 1 and FIG. 2 illustrate the double jersey knits 112 and single jersey knits 114 knitted on the fabric body 102 and continuous channel 104, respectively. It will be appreciated that the double jersey knitting process is a form of knitting in which a plurality of fabrics are knitted simultaneously on one pair of needles. The double jersey knitting process is performed using a double bed knitting machine.

In some other embodiments, the fabric body 102 is a circular knitted fabric that may be formed or knitted by a single jersey knitting process. The continuous channel 104 may formed or knitted within the fabric body 102 by tuck and miss loops.

In one embodiment of the step 206, the insulated conductive element 106 is disposed, e.g. by laying or weaving, within the continuous channel 104 while the fabric body 102 and continuous channel 104 are being formed or knitted, i.e. while using the same knitting machinery. An in-layering technique in the double jersey knits of the fabric body 102 may be used to incorporate or lay the insulated conductive element 106 into the fabric body 102 at yarn level, thereby giving the fabric body 102 a seamless finish and enhancing the visual aesthetics of the textile 100. The seamless integration of the insulated conductive element 106 within the fabric body 102 at yarn level forms a single layer textile 100, enhancing breathability of the textile 100 and improving comfort to users, e.g. wearers of garments made of the textile 100.

In another embodiment of the step 206, the insulated conductive element 106 is disposed within the continuous channel 104 by insertion into the continuous channel 104 after the fabric body 102 and continuous channel 104 have been formed or knitted. Specifically, the fabric body 102 is knitted with spaces for forming or knitting the continuous channel 104. The insulated conductive element 106 is then inserted into the continuous channel 104 after the fabric body 102 is knitted.

Figure 5:
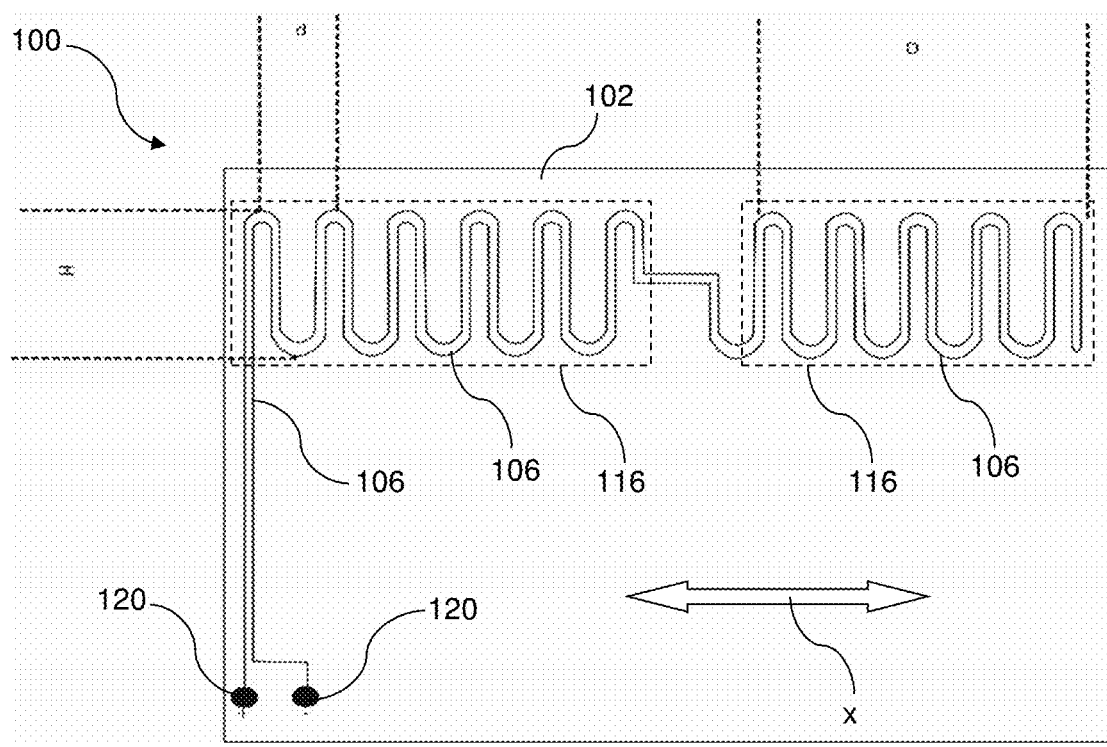
FIG. 5 is an illustration of a front view of the textile showing the arrangement of the insulated conductive element, in accordance with embodiments of the present disclosure.

In some embodiments with reference to FIG. 5, the textile 100 is heatable at one or more regions 116 of the fabric body 102. Specifically, insulated conductive element 106 is disposed in predefined arrangements at the one or more regions 116 of the fabric body 102. As shown in FIG. 5, the fabric body 102 has two regions 116 that are heatable by the insulated conductive element 106. The regions 116 may also be referred to as heating regions/places/panels. The regions 116 define the heating area of the textile 100 and the heating area can be customized by the user based on user requirement or end application of the textile 100, such as by varying the design (e.g. size and shape) of the regions 116.

Each predefined arrangement may be a sinusoidal arrangement of the insulated conductive element 106 at the respective regions 116 of the fabric body 102. In each sinusoidal arrangement or pattern as shown in FIG. 5, there is a spacing d between successive peaks of the sinusoidal arrangement. The spacing d is determined in a way to achieve uniform distribution of heat within that specific region 116. The total length of each sinusoidal arrangement is indicated as D, and the height (from trough to peak) of each sinusoidal arrangement is indicated as H. The sinusoidal arrangement of the insulated conductive element 106 at the regions 116 advantageously facilitates stretching of the textile 100 along a stretching direction x as indicated in FIG. 5.

In some other embodiments, instead of a sinusoidal arrangement or pattern, other predefined arrangements or patterns may be used for disposing the insulated conductive element 106 at the regions 116, such as a serpentine, spiral, curvilinear, zigzag, and wave-like patterns. Particularly, the predefined arrangements of the insulated conductive element 106 are such that stretchability of the textile 100 is not affected along at least the stretching direction x. The predefined arrangements of the insulated conductive element 106 are thus based on factors that relate to the stretchability of the textile 100, and may further relate to restriction of movement of the in-lay feeder in the double bed knitting machine.

Figure 6:
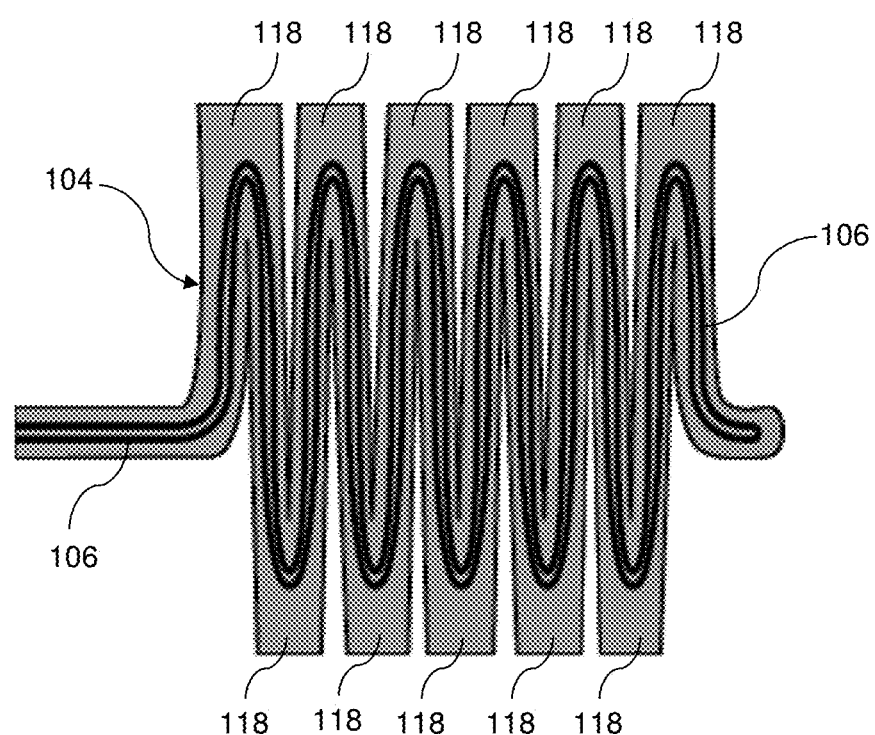
FIG. 6 is an illustration of the insulated conductive element disposed within a continuous channel of the textile in accordance with embodiments of the present disclosure.

In some embodiments with reference to FIG. 6, when the continuous channel 104 is being formed or knitted, additional spacings 118 are formed within the continuous channel 104 as engineering tolerances to facilitate free movement of the insulated conductive element 106 within the continuous channel 104. Notably, the internal cross-sectional diameter or width of the continuous channel 104 is larger than the cross-sectional diameter or width of the insulated conductive element 106. For example, the internal cross-sectional width of the continuous channel 104 may be proportional to the cross-sectional width of the insulated conductive element 106. The internal cross-sectional width of the continuous channel 104 may range, as a non-limiting example, from 1 mm to 100 mm. The additional spacings 118 improve the stretchability of the textile 100. Specifically, when the textile 100 is stretched, such as along the stretching direction x, the additional spacings 118 allow the insulated conductive element 106 to widen within the additional spacings 118. The spacings d between successive peaks of the sinusoidal arrangements increase when the textile 100 is stretched.

In one embodiment, the length of the insulated conducive element 106 disposed within the continuous channel 104 is the same as the length of the continuous channel 104. In another embodiment, the insulated conductive element 106 is disposed within the continuous channel 104 in a slack condition, i.e. not in tension. Specifically, the insulated conductive element 106 is longer than the continuous channel 104, e.g. more than twice as long. With the additional length of the insulated conductive element 106 over the continuous channel 104, the insulated conductive element 106 would not be in tension when the textile 100 is finished. Furthermore, when the textile 100 is stretched, the additional length of the insulated conductive element 106 prevents or mitigates risk of the insulated conductive element 106 breaking, such as due to excessive tension forces resulting from said stretching.

In some embodiments with reference to FIG. 5, the insulated conductive element 106 has an elongated profile with two ends 120. The two ends 120 represent the positive and negative terminals of the insulated conductive element 106. The textile 100 may optionally comprise an electrical interconnection or power connector connected to the ends 120 of the insulated conductive element 106. Correspondingly, the method 200 may optionally comprise a step of connecting a power connector to the ends 120 of the insulated conductive element 106. The power connector is connectable to a power source for supplying the electrical current to the insulated conductive element 106.

The power connector may be partially exposed from the textile 100 to enable the user to connect the power source to the power connector, and conversely to disconnect the power source from the power connector. Accordingly, the user may be able to connect and disconnect the power source on demand. By connecting the power source to the ends 120 of the insulated conductive element 106, a closed electrical circuit is formed between the power source and the insulated conductive element 106, thereby enabling the electrical current to flow along the insulated conductive element 106. A continuous conductive pathway is thus formed between the ends 120 of the insulated conductive element 106. It can be seen that part of the insulated conductive element 106 is used as a conductive pathway for carrying the electrical current from the power source to the regions 116. There are no separate electrical wires connected to the insulated conductive element 106 to function as conductive pathways.

In some embodiments with reference to FIG. 5, the insulated conductive element 106 is continuously laid or routed within the fabric body 102 without using any other conductive pathways to carry the electrical current from the power source. As a single continuous conductive pathway is used in the fabric body 102, the whole insulated conductive element 106 is heatable when the electrical current flows therethrough.

The insulated conductive element 106 is disposed in predefined arrangements at the regions 116 to improve the heating efficiencies of the regions 116. For each region 116, the heating efficiency is dependent, e.g. directly proportional, to the ratio of (A) the length of the insulated conductive element 106 within the region 116 to (B) the length of the insulated conductive element 106 used as a conductive pathway for carrying the electrical current from the power source to the region 116. Notably, the length of the insulated conductive element 106 outside the regions 116 is considered as being used as the conductive pathway. For example, at least 80% of the total length of the insulated conductive element 106 resides within the regions 116, while the remaining portion of the insulated conductive element 106 is being used as the conductive pathway for carrying the electrical current.

The insulated conductive element 106 may have an electrical resistance ranging, as a non-limiting example, from 0.1 to 200 ohms per metre. The total electrical resistance for each region 116 may range, as a non-limiting example, from 0.1 to 200 ohms per square centimetre. The input voltage for each region 116 may range, as a non-limiting example, from 1 to 15 V. The output power for each region 116 may range, as a non-limiting example, from 5 to 25 W.

As described above, the textile 100 may comprise a power connector for connecting to the power source. The power connector may be a DC jack for receiving direct current from the power source. The power connector may include a snap-and-lock configuration for quick and secure connection of the power source thereto. It will be appreciated that other types of power connectors may be used, and the power connector may vary in size and form factor, such as depending on the various characteristics/properties/purposes/usages of the textile 100. For example, the power connector may be dependent on whether the textile 100 is used for apparel or electronics. For apparel usage, pieces of garments or clothing made of the textile 100 can be joined together using connections that are modified to additionally function as the power connector, as will be readily understood by the skilled person. For example, the power connector may use conductive hook-and-loop fasteners (e.g. of the Velcro® brand), bar tagging, snaps, or conductive zips. For electronics usage, the power connector may use lugs and soldering, as will be readily understood by the skilled person.

The power source or external power supply supplies the electrical energy needed by the textile 100 to heat up the insulated conductive element 106. Heat is generated in the insulated conductive element 106, and thus in the textile 100, by supplying electrical current to the insulated conductive element 106. The power source may be a portable power bank/source/module, such as a battery. Alternatively, the power source may be a direct power source from a main power supply via a standard wall socket. Further alternatively, the power source may be sourced through energy harvesting. Particularly, harvested energy is stored in a capacitor and/or battery which are later used to power the insulated conductive element 106. Energy may be harvested from solar energy, kinetic energy, wind energy, thermal energy, and salinity gradient energy, as will be readily understood by the skilled person.

The power source may optionally include a heat controller to control the electrical current flowing to the insulated conductive element 106, thereby regulating the amount of heat generated in the textile 100. The heat controller may provide a plurality of predefined settings, such as three distinct settings associated with three different heat or temperature levels—high, medium, and low.

Various embodiments of the present disclosure thus describe the textile 100 and a method 200 of manufacturing the textile 100. The textile 100 is heatable when electrical current flows through the insulated conductive element 106 of the textile 100. The textile 100 may thus be referred to a heating textile and may be used in garments. When a user wears a garment made of the textile 100 and the insulated conductive element 106 is heated up, the textile 100 provides thermal comfort to the user. The fabric body 102 of the textile 100 may be formed from a passive heating yarn with heat retention characteristics. The textile 100 thus uses active heating from the insulated conductive element 106, as well as passive heating from the passive heating yarn. The combination of said active heating and passive heating enhances the heating characteristics/properties of the textile 100. Furthermore, with the heat retention characteristics of the passive heating yarn, the electrical energy to be supplied from the power source to the insulated conductive element 106 may be reduced, thereby improving the efficiency and lifespan of the power source. Yet furthermore, the textile 100 retains the conventional properties of fabric textiles, including it being launderable (durable for washing), breathable, drapeable, and stretchable.

Figure 7:
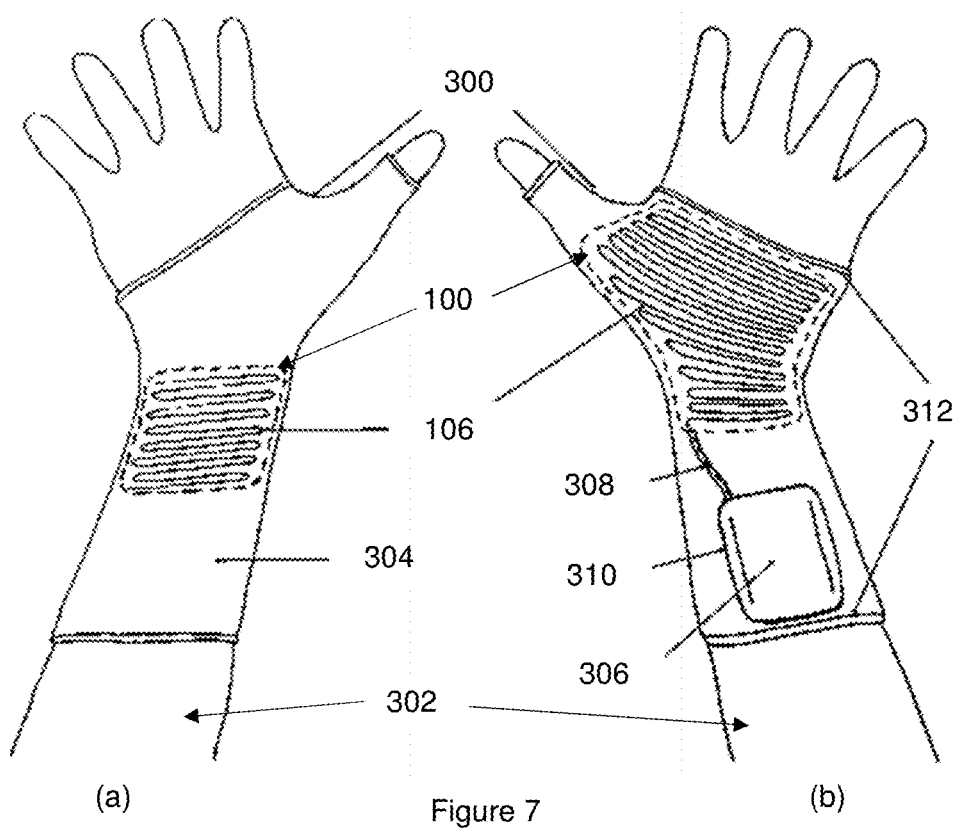
FIG. 7 is an illustration of the textile incorporated into a glove wearable on a person's arm, in accordance with embodiments of the present disclosure.

One possible end application of the heatable textile 100 is a glove 300 wearable on a person's arm 302 as shown in FIG. 7. The arm 302 includes the forearm, wrist, and hand.

FIG. 7a illustrates the bottom side of the arm 302 wearing the glove 300 and FIG. 7b illustrates the top side of the arm 302. The glove 300 may be in the form of a fingerless glove or a hand/wrist wrap/sleeve that covers the arm 302 from the base of the fingers to the wrist and could extend till the elbow. Extending the glove 300 over a large portion of the arm 300 would cover the extensor tendons, tendon sheath, and the extensor retinaculum. The glove 300 may be designed as a gaming accessory and form-fitting to the person or user wearing it, so that the user is able to perform gaming tasks such as holding/manipulating other gaming devices, such as but not limited to, gaming controllers, mice, and joysticks.

The glove 300 is made of the textile 100 comprising the heatable insulated conductive element 106. The heatable textile 100 is incorporated in the material 304 of the glove 300 so that the glove 300 is configured for improving blood circulation in the arm 302 which can help to relax tendons and muscles in the arm 302, particularly at in the hand and especially for users with chronic wrist and hand pain. The glove 300 may be used to treat various arm wrist ailments/conditions (including of the wrist) such as but not limited to, tendonitis, carpal tunnel syndrome, and de Quervain's syndrome.

The glove 300 includes a power source or battery module 306 for heating the insulated conductive element 106 embedded in the glove 300 and consequently warm the arm 302 including the wrist. The battery module 306 is connected to the insulated conductive element 106 via a power connector or port 308. The battery module 306 is designed to be small and lightweight so that the glove 300 is less strenuous for the user wearing it. The battery module 306 is also removable so that it can be easily replaced. The glove 300 includes a hidden or discreet pocket 310 for holding the battery module 306. The glove 300 further includes a heat controller to regulate the heat generated by the glove 300. For example, the heat controller allows the user to regulate the temperature for preferred comfort and treatment of conditions. The controllable temperature may range from 37° C. to 55° C., although other temperature ranges are possible.

The glove 300 is an engineered knit in order to secure it to the contour of the arm 302 including the hand and wrist. This prevents excessive movement of the glove's material 304 during the user's hand movements and also supports the wrist from excessive bending. In addition to the heatable textile 100, the glove's material 304 further includes synthetic and metallic yarns that are moisture-wicking and thermally conductive. The glove 300 may provide compression to support the tendons and muscles of the arm 302, especially at the hand and wrist. The compression pressure may be in the region of 8 mmHg to 19 mm Hg, although other ranges are possible. It is also possible that the glove 300 provides medical grade compression, as will be readily understood by the skilled person. The ends 312 of the glove 300 have hidden seams which provide a contoured fit and compression to the user.

Figure 8A:
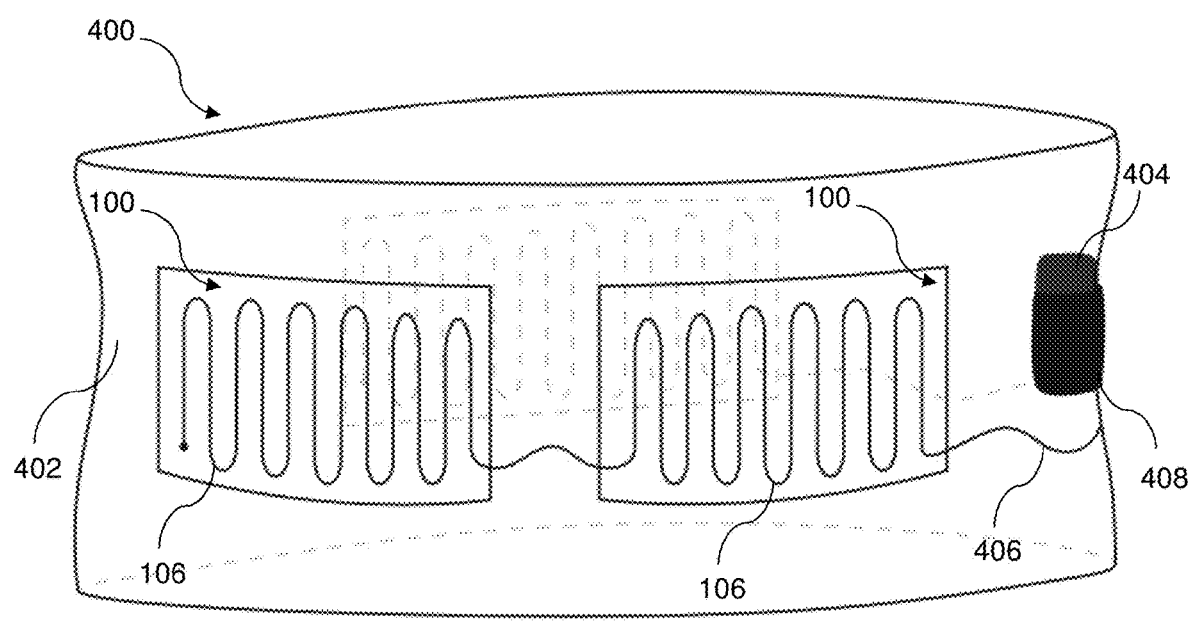
FIG. 8a to FIG. 8c are illustrations of the textile incorporated into a band wearable around a woman's belly region, in accordance with embodiments of the present disclosure.
Figure 8B:
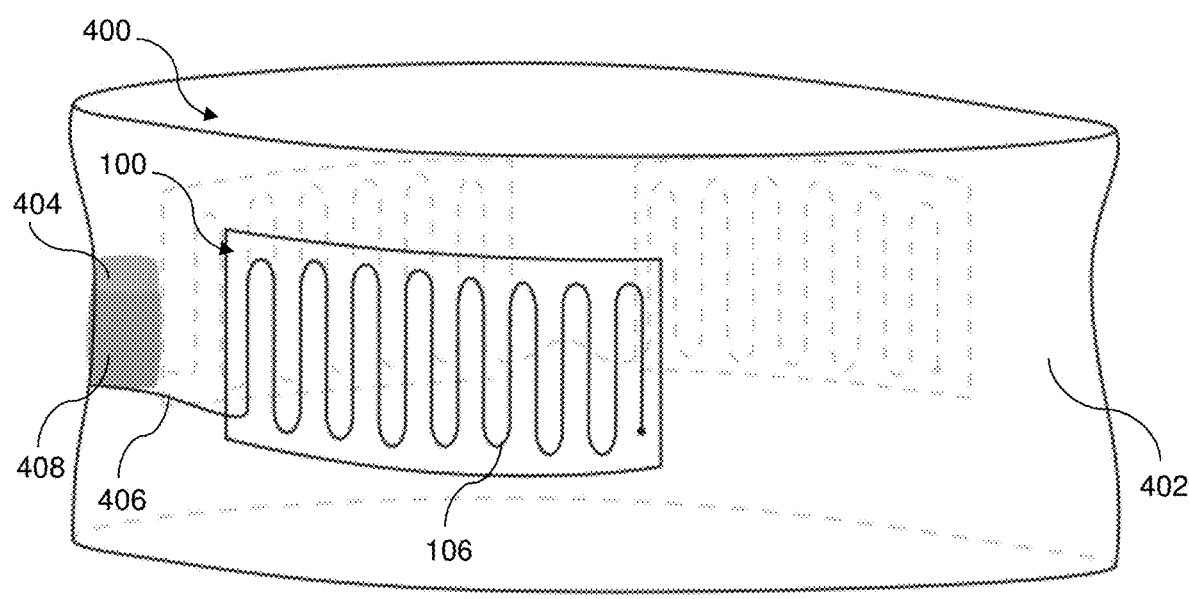
Figure 8C:
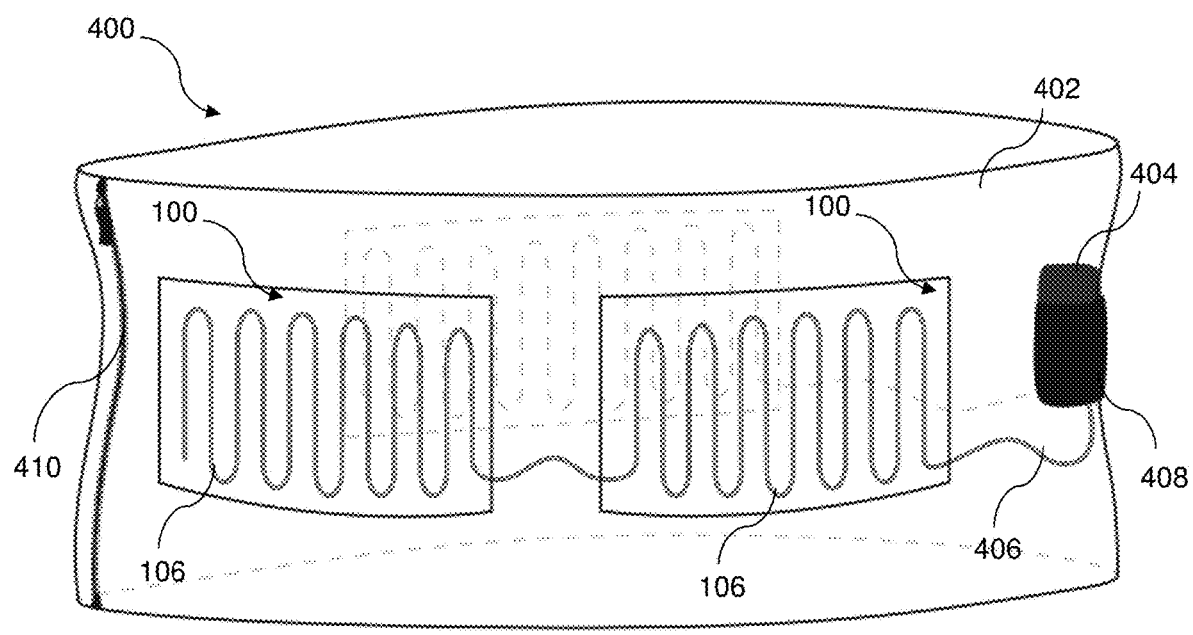

Another possible end application of the heatable textile 100 is a band 400 wearable around a woman's belly region and/or lower back region as shown in FIG. 8a to FIG. 8c. FIG. 8a illustrates the front view of the band 400, FIG. 8b illustrates the back view of the band 400, and FIG. 8c illustrates the band 400 with an attachment mechanism (described below). The band 400 may be in the form of a belly band, belly wrap, or a high waist panty covering the belly region and lower back region, specifically the lower abdomen and lower back.

The band 400 is made of the textile 100 comprising the heatable insulated conductive element 106. The heatable textile 100 is incorporated in the material 402 of the band 400 so that the band 400 is configured for improving blood circulation in the belly region and/or the lower back region. The heat and compression provided by the band 400 helps to relief menstrual pain and/or lower back pain, specifically by relaxing the myometrium, reducing constriction of blood vessels, and improving blood flow to the uterus.

The band 400 includes a power source or battery module 404 for heating the insulated conductive element 106 embedded in the band 400 and consequently warm the belly region. The battery module 404 is connected to the insulated conductive element 106 via a power connector or port 406 and the battery module 404 is supported in a pocket 408. The band 400 further includes a heat controller to regulate the heat generated by the band 400. Additionally, to help the user wear the band 400, the band 400 includes an attachment mechanism 410 at the edges thereof. The attachment mechanism 410 may include, but is not limited to, zippers, hook-and-loop fasteners, hook-and-eye fasteners, magnetic connectors, or Boa closure system, as will be readily known to the skilled person.

In the foregoing detailed description, embodiments of the present disclosure in relation to a textile and a manufacturing method thereof are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A textile comprising:
   a fabric body formed from one or more types of yarns;
   a continuous channel formed within the fabric body, the continuous channel in a sinusoidal arrangement along a stretching direction of the fabric body;
   an insulated conductive element freely disposed in a slack condition and in a sinusoidal arrangement within the continuous channel; and
   spacings formed within the continuous channel to facilitate free movement of the insulated conductive element within the continuous channel,
   wherein the spacings allow the insulated conductive element to widen within the spacings and improve stretchability of the textile along the stretching direction; and
   wherein the textile is heatable in response to electrical current being conducted through the insulated conductive element.

2. The textile according to claim 1, wherein the textile is heatable at one or more regions of the fabric body.

3. The textile according to claim 2, wherein the continuous channel and the insulated conductive element are disposed in sinusoidal arrangements at the one or more regions of the fabric body.

4. The textile according to claim 1, further comprising a power connector connected to ends of the insulated conductive element, the power connector connectable to a power source for supplying the electrical current.

5. The textile according to claim 1, wherein the fabric body and the continuous channel are formed by knitting.

6. The textile according to claim 5, wherein the fabric body is knitted by a double jersey knitting process and the continuous channel is knitted within the fabric body by a single jersey knitting process.

7. The textile according to claim 1, wherein the one or more types of yarns comprises a passive heating yarn and/or a normal yarn.

8. The textile according to claim 7, wherein the passive heating yarn comprises an infrared yarn and/or a yarn made of a phase change material.

9. The textile according to claim 7, wherein the normal yarn comprises one or more of nylon yarn, polyester yarn, and spandex yarn.

10. A glove wearable on a person's arm and configured for improving blood circulation in the arm, the glove comprising the heatable textile according to claim 1.

11. A band wearable around a woman's belly region and/or lower back region and configured for improving blood circulation in the belly region and/or lower back region, the band comprising the heatable textile according to claim 1.

12. A method of manufacturing a textile, the method comprising:
    forming a fabric body from one or more types of yarns;
    forming a continuous channel within the fabric body, the continuous channel in a sinusoidal arrangement along a stretching direction of the fabric body; and
    disposing an insulated conductive element freely in a slack condition, and in a sinusoidal arrangement within the continuous channel,
    wherein spacings are formed within the continuous channel to facilitate free movement of the insulated conductive element within the continuous channel,
    wherein the spacings allow the insulated conductive element to widen within the spacings and improve stretchability of the textile along the stretching direction; and
    wherein the textile is heatable in response to electrical current being conducted through the insulated conductive element.

13. The method according to claim 12, wherein the textile is heatable at one or more regions of the fabric body.

14. The method according to claim 13, wherein the continuous channel and the insulated conductive element are disposed in sinusoidal arrangements at the one or more regions of the fabric body.

15. The method according to claim 12, wherein the fabric body and the continuous channel are formed by knitting.

16. The method according to claim 15, wherein the insulated conductive element is disposed within the continuous channel during said knitting of the fabric body and the continuous channel.

17. The method according to claim 15, wherein the insulated conductive element is disposed within the continuous channel by insertion into the continuous channel after the fabric body is knitted.

* * * * *